(12) United States Patent
Macias

(10) Patent No.: US 6,340,699 B1
(45) Date of Patent: Jan. 22, 2002

(54) SPLA$_2$ INHIBITOR COMPOUNDS FOR TREATMENT OF DISEASE

(75) Inventor: William Louis Macias, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/673,675

(22) PCT Filed: Apr. 20, 1999

(86) PCT No.: PCT/US99/08654

§ 371 Date: Oct. 17, 2000

§ 102(e) Date: Oct. 17, 2000

(87) PCT Pub. No.: WO99/57100

PCT Pub. Date: Nov. 11, 1999

Related U.S. Application Data
(60) Provisional application No. 60/083,874, filed on May 1, 1998.

(51) Int. Cl.$^7$ ............................................... A61K 31/40
(52) U.S. Cl. ...................................................... 514/419
(58) Field of Search ........................................ 514/419

(56) References Cited

U.S. PATENT DOCUMENTS

| 5,654,326 A | 8/1997 | Bach et al. |
| 5,716,983 A | 2/1998 | Friebe et al. |

FOREIGN PATENT DOCUMENTS

| EP | 0 675110 A1 | 10/1995 |
| EP | 0 799836 A1 | 10/1997 |
| WO | WO 92/21644 A | 12/1992 |
| WO | WO 93/24492 A | 12/1993 |
| WO | WO 98/18464 | 5/1998 |

OTHER PUBLICATIONS

Peterson, et al., Gut, 39(5) : p. 698–704 (1996).
Murthy, et al., Inflammation 16(3) : p. 259–271 (1992).
Hastings, et al., Am. Famil. Physician 47(3), p. 598–608 (1993).

*Primary Examiner*—Raymond Henley, III
(74) *Attorney, Agent, or Firm*—Roger S. Benjamin

(57) ABSTRACT

The present invention is directed to compounds for treating inflammatory bowel disease. More specifically, the present invention is directed to 1H-indole-3-glyoxyamide compounds a sPLA$_2$ inhibitors for treating inflammatory bowel disease.

12 Claims, No Drawings

SPLA₂ INHIBITOR COMPOUNDS FOR TREATMENT OF DISEASE

This application is a 371 of PCT/US99/08654 filed Apr. 20, 1999 which claims priority to U.S. Provisional Application No. 60/083,874 filed May 1, 1998.

FIELD OF THE INVENTION

The present invention is directed to compounds for treating inflammatory bowel disease. More specifically, the present invention is directed to 1H-indole-3-glyoxylamide compounds as sPLA₂ inhibitors for treating inflammatory bowel disease.

BACKGROUND OF THE INVENTION

Inflammatory bowel disease (IBD) is a term that classifies a group of chronic inflammatory disorders involving the gastrointestinal tract. While the exact cause of these diseases are unknown, they exhibit features that permit diagnosis in most cases. Inflammatory bowel disease is inclusive of two main disease states: ulcerative colitis(UC) and Crohn's disease(DC). The possible treatment effects of sPLA₂ inhibitor compounds on ulcerative colitis and Crohn's disease states have been variously enumerated(see, Peterson, et al., *Gut,* 39(5): 698–704 (1996), Murthy, et al., *Inflammation* 16(3): 259–71 (1992), Hastings, et al.,*Am. Famil. Physician* 47(3): 598–608 (1993)).

Claims to the use of sPLA₂ inhibitors can be found in the following patent documents: WO 98/18464; WO 96/20959; WO 95/02588A; WO 93/24492A; WO 92/21644A; European Patent Apln. Publ. no. 0675110.

Possible causes that have been advanced for IBD include genetic, infectious, immunologic and psychological. While the exact etiology of the disease is unknown, it is believed that the manifestation of this disease state is a result of immune response within the epithelial and/or the endothelial cells in the colon to external stimuli.

Ulcerative colitis involves an inflammatory reaction affecting the colon. The colon appears ulcerated and hemorrhaged. The inflammation is generally uniform and continuous and often involves the rectum. The major symptoms of ulcerative colitis include bloody diarrhea or constipation, abdominal pain, signs of dehydration, anemia, fever and weight loss. Extracolonic manifestations may include athritis, evidence of liver disease, skin disease and lung disease.

Crohn's disease is characterized by inflammation extending through all layers of the intestinal wall and often including the mesenteric lymph nodes. The inflammations may penetrate the mucosa and coalesce to form channels called fistulas and fissures. In Crohn's disease inflammations of the bowel are often discontinues and often granulomatous (see Harrison's *Principles of Internal Medicine,* thirteenth ed., 1994, by McGraw-Hill, Inc., ISBN 0-07-032370-4, pg., 1403–1416).

Treatment options include surgical removal of affected tissue often with attendant reconstructive procedures to enable waste removal. Surgical procedures are expensive, inconvenient and often not curative as relapses and new infected sites may be manifested. Medical treatments include but are not limited to administration of corticosteroids, sulfasalazine, 5-amino salicylic acids (5-ASA,), azathioprene, 6-mercaptopurine (6-MP). These treatments are focused on the amelioration of the inflammatory response.

There is a great need for specific and effective treatment of IBD (Sutherland *CMAJ* 137; 799–802, 1987).

It is an object of the present invention to provide a new methodology for effective treatment of inflammatory bowel disease.

SUMMARY OF THE INVENTION

This invention is for the treatment of inflammatory bowel disease in a mammal, including a human, by administering a therapeutically effective amount of 1H-indole-3-glyoxylamide sPLA₂ inhibitors.

This invention is also a method for preventing inflammatory bowel disease in a mammal, including a human, by administering a therapeutically effective amount of an 1H-indole-3-glyoxylamide sPLA₂ inhibitor.

This invention is also the use of 1H-indole-3-glyoxylamide sPLA2 inhibitors to reduce the complications of acute or chronic infections of the intestine in a human afflicted with gastric and duodenal ulcers adjunctive to inflammatory bowel disease.

This invention is also a method for the treatment of a mammal, including humans, afflicted with inflammatory bowel disease by the use of 1H-indole-3-glyoxylamide sPLA₂ inhibitors in combination with other IBD treatment compounds.

This invention is also the use of 1H-indole-3-glyoxylamide sPLA₂ inhibitor compounds for the manufacture of medicaments for the treatment of inflammatory bowel disease.

This invention is also a formulation for treatment of IBD comprising (i) an 1H-indole-3-glyoxylamide sPLA₂ inhibitor; and (ii) one or more other IBD treatment compounds; and (iii) a carrier or diluent

DETAILED DESCRIPTION OF THE INVENTION

Definitions
General Definitions

The term, "inflammatory bowel disease" (abbreviated IBD) includes the disease states of (i) ulcerative colitis, (ii) Crohn's disease, and (iii) symptoms of IBD inclusive of associated inflammation, ulcers and infections.

The term, "therapeutically effective amount" is a quantity of 1H-indole-3-glyoxylamide SPLA2 inhibitor sufficient to significantly alleviate symptoms of inflammatory bowel disease in a mammal.

The term, "parenteral" means not through the alimentary canal but by some other route such as subcutaneous, intramuscular, intraorbital, intracapsular, intraspinal, intrasternal, or intravenous.

The term, "active compound" means one or more sPLA₂ inhibitors used in the method of the invention.

The term "IBD treatment compounds" means compounds other than 1H-indole-3-glyoxylamide sPLA₂ inhibitors which are conventionally used for treatment of IBD, including but not limited to corticosteroids, sulfasalazine, 5-aminosalicylic acids (5-ASA), 6-mercaptopurine (6-MP), azathioprene.

I. SPLA₂ Inhibitors useful in the Mehtod of the Invention 1H-indole-3-glyoxylamide secretary phospholipase A2 (sPLA₂) inhibitors are useful in the practice of the method of this invention. The 1H-indole-3-glyoxylamide sPLA2 inhibitors and method of making them are described in U.S. Pat. No. 5,654,326, the disclosure of which is incorporated herein by reference. These 1H-indole-3-glyoxylamide compounds are also described in European Patent Application No. 95302166.4, Publication No. 0 675 110 (publ., Oct. 4, 1995). Definitions for 1H-indole-3-glyoxylamide compounds:

The words, "acid linker" refers to a divalent linking group of the 1H-indole-3-glyoxylamide compounds is symbolized as, —($L_a$)—, which has the function of joining the 4 or 5 position of the indole nucleus to an acidic group in the general relationship:

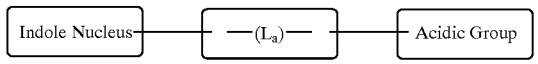

The words, "acid linker length", refer to the number of atoms (excluding hydrogen) in the shortest chain of the linking group —($L_a$)— that connects the 4 or 5 position of the indole nucleus with the acidic group.

Preferred 1H-indole-3-glyoxylamide sPLA$_2$ inhibitors for practicing the method of the invention (and preparing formulations of the invention) are represented by formula (I), or a pharmaceutically acceptable salt or prodrug derivative thereof;

(I)

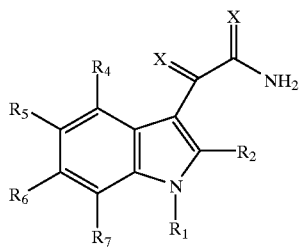

wherein;

both X are oxygen;

$R_1$ is selected from the group consisting of

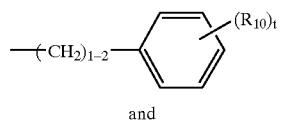

and

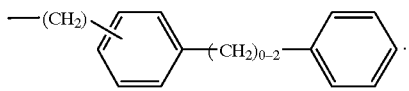

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)-(acidic group); wherein —($L_a$)— is an acid linker; provided, the acid linker group, —($L_a$)—, for $R_4$ is selected from the group consisting of;

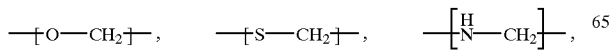

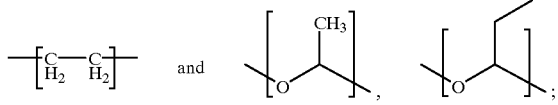

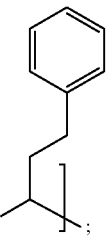

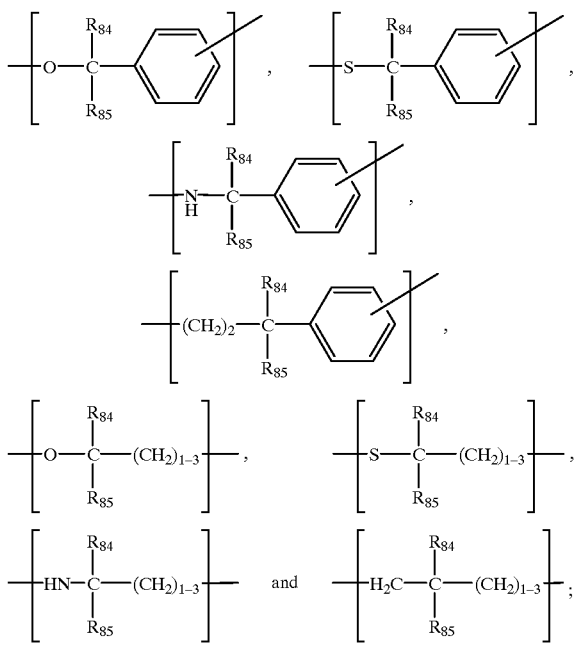

and provided, the acid linker, —($L_a$)—, for $R_5$ is selected from group consisting of;

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2$H, —$SO_3$H, or —P(O) (OH)$_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, phenylmethyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO₃H, thioacetal, thiocarbonyl, and C₁–C₆ carbonyl; where n is from 1 to 8.

Particularly preferred for practicing the method of the invention are 1H-indole-3-glyoxylamide compounds and all corresponding pharmaceutically acceptable salts, solvates and prodrug derivatives thereof which include the following:

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid,
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (P) in any combination.

In general any prodrug derivative any be used. However particularly useful prodrugs of the compounds of formula (I) and named compounds (A) thru (O) are esters, particularly, the simple aromatic and aliphatic esters, such as the methyl, ethyl, propyl, isopropyl, and morpholine-N-ethyl.

Most preferred in the practice of the method of the invention are 1H-indole-3-glyoxylamides selected from the group represented by the formulae:

(Va)

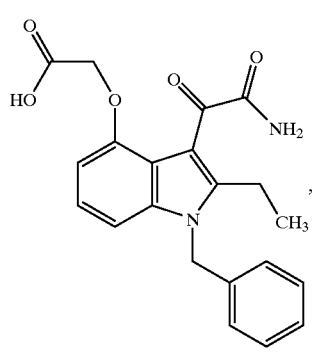

, the methyl ester of (Va)

(Vb)

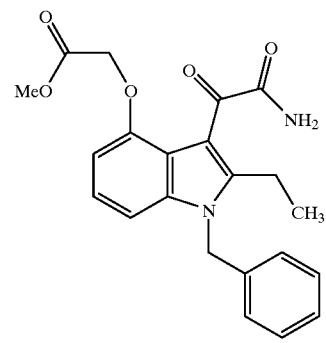

and (Vc)

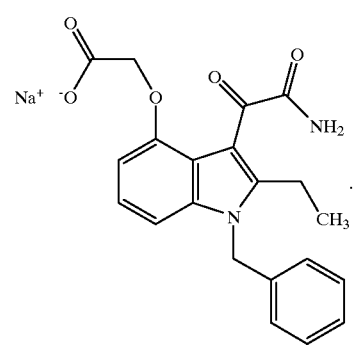

The synthesis of the 1H-indole-3-glyoxylamide compounds used in the method of treating inflammatory bowel disease may be accomplished as described European Patent Application No. 95302166.4, Publication No. 0 675 110 (publ., Oct. 4, 1995). Such synthesis methods also include well-known methods as recorded in the chemical literature and the procedure illustrated in the following preparative reaction scheme:

1H-indole-3-glyoxylamide Reaction Scheme

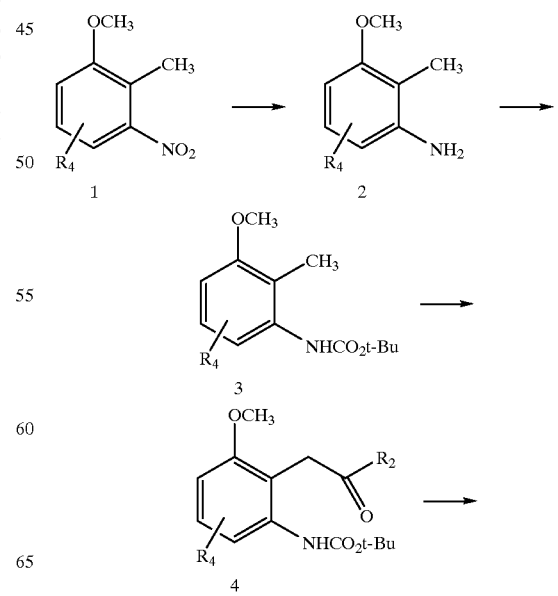

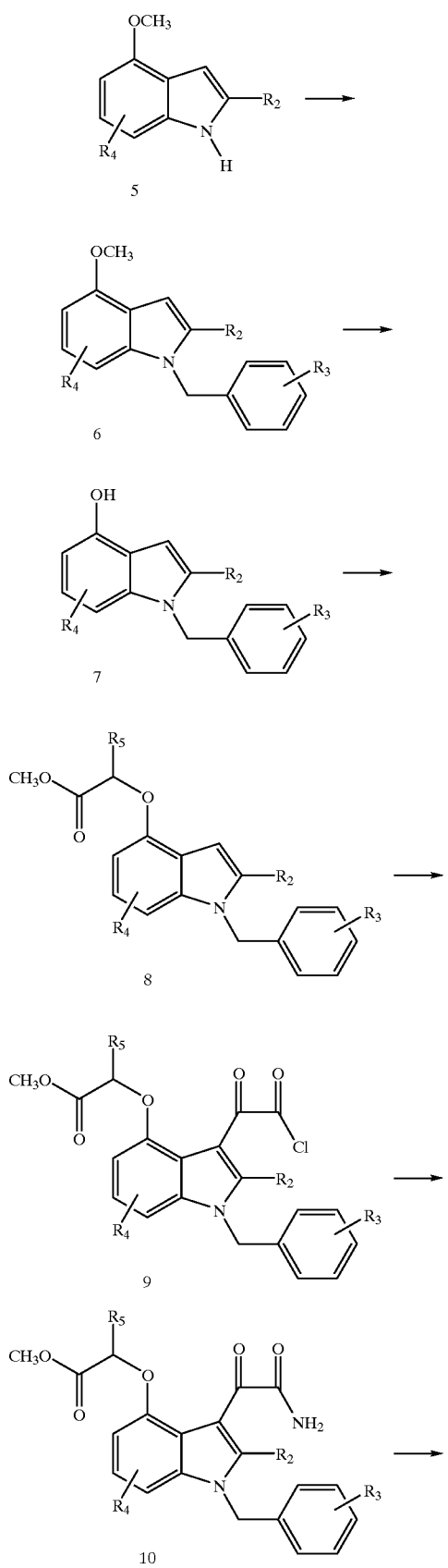

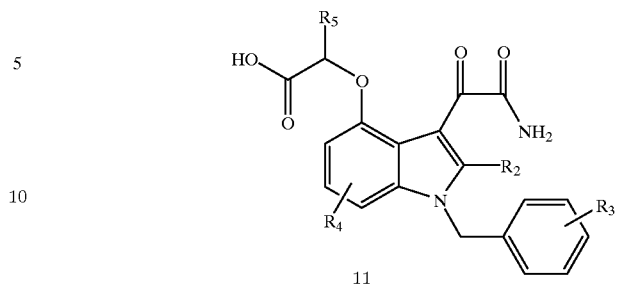

Explanation of Reaction Scheme

To obtain the glyoxylamides substituted in the 4-position with an acidic function through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, *Synthesis,* 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, *Adv. Drug Res.,* 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The a-[(indol-4-yl)oxy]alkanoic acid ester, 8, is reacted with oxalyl chloride in methylene chloride to give 9, which is not purified but reacted directly with ammonia to give the glyoxylamide 10. This product is hydrolyzed using 1N sodium hydroxide in MeOH. The final glyoxylamide, 11, is isolated either as the free carboxylic acid or as its sodium salt or in both forms.

The most preferred compound, [[3-(2-Amino-1,2-dioxoethyl)-2-ethyl-1-(phenylmethyl)-1H-indol-4-yl]oxy] acetic acid (as well as its sodium salt and methyl ester) useful in the practice of the method of the invention, may be prepared by the following procedure:

Preparation of [[3-(2-Amino-1,2-dioxoethyl)-2-ethyl-1-(phenylmethyl)-1H-indol-4-yl]oxy]acetic acid, a compound represented by the formula:

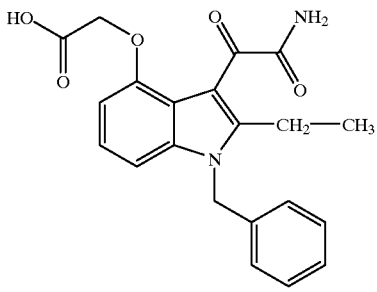

Part A. Preparation of 2-Ethyl-4-methoxy-1H-indole

A solution of 140 mL (0.18 mol) of 1.3M sec-butyl lithium in cyclohexane was added slowly to N-tert-butoxycarbonyl-3-methoxy-2-methylaniline (21.3g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over $MgSO_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried ($MgSO_4$) and concentrated. The residue was chromatographed three times on silica eluting with 20% EtOAc/hexane to give 13.9 g of 2-ethyl-4-methoxy-1H-indole.

Analyses for $C_{11}H_{13}NO$: Calculated: C, 75.40; H, 7.48; N, 7.99 Found: C, 74.41; H, 7.64; N, 7.97.

Part B. Preparation of 2-Ethyl-4-methoxy-1-(phenylmethyl)-1H-indole

2-Ethyl-4-methoxy-1H-indole (4.2 g, 24 mmol) was dissolved in 30 mL of DMF and 960 mg (24 mmol) of 60% NaH/mineral oil was added. After 1.5 hours, 2.9 mL (24 mmol) of benzyl bromide was added. After 4 hours, the mixture was diluted with water and extracted twice with ethyl acetate. The combined ethyl acetate was washed with brine, dried ($MgSO_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole

By the method used in Part B, 3.1 g (11.7 mmol) of 2-ethyl-4-methoxy-1-(phenylmethyl)-1H-indole was O-demethylated by treating it with 48.6 mL of 1M $BBr_3$/$CH_2C_{12}$ to give a material that was chromatographed on silica gel (eluted with 20% EtOAc/hexane) to give 1.58 g (54% yield) of 2-ethyl-4-hydroxy-1-(phenylmethyl)-1H-indole, mp, 86–90° C.

Analyses for $C_{17}H_{17}N$: Calculated: C, 81.24; H, 6.82; N, 5.57 Found: C, 81.08; H, 6.92; N, 5.41.

Part D. Preparation of [[2-Ethyl-1-(phenylmethyl)-1H-indol-4-yl]oxy]acetic acid methyl ester Using the procedure described in Part C, 2-ethyl-4-hydroxy-1-(phenylmethyl)-1H-indole (1.56 g, 6.2 mmol) was treated with 248 mg (6.2 mmol) of 60% NaH/mineral oil and then 0.6 mL(6.2 mmol) of methyl bromoacetate. The product was purified by chromatography over silica gel eluting with 20% EtOAc/hexane, to give 1.37 g (69% yield) of [[2-ethyl-1-(phenylmethyl)-1H-indol-4-yl]oxy]acetic acid methyl ester, 89–92° C.

Analyses for $C_{20}H_{21}NO_3$: Calculated: C, 74.28; H, 6.55; N, 4.33 Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic acid methyl ester Using the procedure in Part D, 1.36 g (4.2 mmol) of [[2-ethyl-1-(phenylmethyl)-1H-indol-4-yl]oxy]acetic acid methyl ester was reacted first with 0.4 mL (4.2 mmol) of oxalyl chloride and then excess ammonia to give a white solid. This was stirred with ethyl acetate and the insoluble material separated and dried to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Part F. Preparation of [[3-(2-Amino-1,2-dioxoethyl)-2-ethyl-1-(phenylmethyl)-1H-indol-4-yl]oxy]acetic acid A mixture of 788 mg (2 mmol) of [3-(2-amino-1,2-dioxoethyl)-2-ethyl-1-(phenylmethyl)-1H-indol-4-yl]oxy]acetic acid methyl ester, 10 mL of in NaOH and 30 mL of MeOH was heated to maintain reflux for 0.5 hour, stirred at room temperature for 0.5 hour and concentrated at reduced pressure. The residue was taken up in ethyl acetate and water, the aqueous layer separated and made acidic to pH 2–3 with 1N HCl. The precipitate was filtered and washed with ethyl acetate to give 559 mg (74% yield) of [[3-(2-amino-1,2-dioxoethyl)-2-ethyl-1-(phenylmethyl)-1H-indol-4-yl]oxy]acetic acid, mp, 230–234° C.

Analyses for $C_{21}H_{20}N_2O_5$: Calculated: C, 65.96; H, 5.80; N, 7.33 Found: C, 66.95; H, 5.55; N, 6.99.

Part G. The sodium salt of the product of Part F, may be formed by reaction with sodium hydroxide (NaOH) and the product isolated by standard laboratory procedures or by use of a sodium charged cation exchange resin.

The morpholino-N-ethyl ester prodrug compound of the invention is prepared by esterification of the acid or salt form of the starting material. Any ester forming method which is conventional in the chemical arts may be used. An exemplary procedure is as follows:

Preparation of ((3-(2-Amino-1,2-dioxoethyl)-1-((1,1'-biphenyl)-3-ylmethyl)-2-methyl-1H-indol-4-yl)oxy)acetic acid, morpholinylethyl ester In a flask containing 10 ml of dimethylformamide is added with stirring 133 mg. of 4-(2-chloroethyl)morpholine hydrochloride (available from Aldrich Chemical Co., Milwaukee, Wis. USA, Item No. C4,220-3) and 231 mg. of CsCO₃ and 300 mg. of ((3-(2-amino-1,2-dioxoethyl)-1-((1,1'-biphenyl)-3-ylmethyl)-2-ethyl-1H-indol-4-yl)oxy)acetic acid, sodium salt. The slurry is heated to 60° C. until a solution formed. Heating is continued overnight until reaction is complete. 20 ml of H₂O is added to the flask and the organic soluble phase is extracted with three 20 ml. portions of ethyl acetate. The ethyl acetate solution is washed with water and dried over Na₂SO₄.

Formulations Suitable for use in the Method of the Invention

The sPLA₂ inhibitors used in the method of the invention may be administered to treat inflammatory bowel disease by any means that produces contact of the active agent with the agent's site of action in the human body. They can be administered by any conventional means available for use in conjunction with pharmaceuticals, either as individual therapeutic agents or in a combination of therapeutic agents. The sPLA₂ inhibitors can be administered alone, but are generally administered with a pharmaceutical carrier selected on the basis of the chosen route of administration and standard pharmaceutical practice.

Suitable formulations are those comprising a therapeutically effective amount of sPLA₂ inhibitor together with a pharmaceutically acceptable diluent or carrier, the composition being adapted for the particular route of administration chosen. By "pharmaceutically acceptable" it is meant the carrier, diluent or excipient must be compatible with the sPLA₂ inhibitor ("active compound") in the formulation and not deleterious to the subject being treated.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the sPLA₂ inhibitor is mixed with a carrier having the necessary binding properties in suitable proportions and compacted in the shape and size desired. The powders and tablets preferably contain from about 1 to about 99 weight percent of the sPLA₂ inhibitor.

Sterile liquid form formulations include suspensions, emulsions, syrups and elixirs. The active compound can be dissolved or suspended in a pharmaceutically acceptable carrier, such as sterile water, saline, dextrose solution, sterile organic solvent or a mixture of both.

The active compound can be administered orally in solid dosage forms, such as capsules, tablets, and powders, or in liquid dosage forms, such as elixirs, syrups, and suspensions. It can also be administered parenterally, in sterile liquid dosage forms. It can also be administered by inhalation in the form of a nasal spray. It can also be administered topically as an ointment, cream, gel, paste, lotion, solution, spray, aerosol, liposome, or patch. Dosage forms used to administer the active compound usually contain suitable carriers, diluents, preservatives, or other excipients, as described in Remington's Pharmaceutical Sciences, Mack Publishing Company, a standard reference text in the field.

Gelatin capsules may be prepared containing the active compound and powdered carriers, such as lactose, sucrose, mannitol, starch, cellulose derivatives, magnesium stearate, stearic acid, and the like. Similar diluents can be used to make compressed tablets and powders. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

For parenteral solutions, water, a suitable oil, saline, aqueous dextrose (glucose), and related sugar solutions and glycols such as propylene glycol or polyethylene glycols are suitable carriers for parenteral solutions. Solutions for parenteral administration contain the active compound, suitable stabilizing agents, and if necessary, buffer substances. Anti-oxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Topical ointments, creams, gels, and pastes contain with the active compound diluents such as waxes, paraffins, starch, polyethylene glycol, silicones, bentonites, silicic acid, animal and vegetable fats, talc and zinc oxide or mixtures of these or other diluents.

Topical solutions and emulsions can, for example, contain with the active compound, customary diluents (with the exclusion of solvents having a molecular weight below 200 except in the presence of a surface-active agent), such as solvents, dissolving agents and emulsifiers; specific examples are water, ethanol, 2-propanol, ethyl carbonate, benzyl alcohol, propylene glycol, oils, glycerol, and fatty acid esters of sorbitol or mixtures thereof. Compositions for topical dosing may also contain preservatives or antioxidizing agents.

Powders and sprays can contain along with the active compound, the usual diluents, such as lactose, talc, silicic acid, aluminum hydroxide, calcium silicate, and polyamide powders or mixtures of these materials. Aerosol sprays can contain the usual propellants. Liposomes can be made from such materials as animal or vegetable fats which will form lipid bilayers in which the active compound can be incorporated.

Formulations containing compounds of the invention may be administered through the skin by an appliance such as a transdermal patch. Patches can be made of a matrix such as polyacrylamide and a semipermeable membrane made from a suitable polymer to control the rate at which the material is delivered to the skin. Other suitable transdermal patch formulations and configurations are described in U.S. Pat. Nos. 5,296,222 and 5,271,940, the disclosures of which are incorporated herein by reference. Lipophilic prodrug derivatives of the sPLA₂ inhibitors are particularly well suited for transdermal absorption administration and delivery systems.

Formulations within the scope of this invention include the admixture of sPLA₂ inhibitor with a therapeutically effective amount of any therapeutically effective co-agents for inflammatory bowel disease including but not limited corticosteroids, sulfasalazine, 5-amino salicylic acids (5-ASA) which have been claimed to be useful in the treatment, amelioration and/or prevention of intestinal bowel disease and/or related physiological conditions as set out in the section "CO-AGENT—COMBINED THERAPY", infra.

For all of the above formulations the preferred active compound are the 1H-indole-3-glyoxylamide compounds as previously described and methods of making as described in n U.S. Pat. No. 5,654,326 (the disclosure of which is incorporated herein by reference). Most preferred compounds within the general class of 1H-indole-3-glyoxylamides are ((3-(2-amino-1,2-dioxoethyl)-2-ethyl-1-(phenylmethyl)-1H-indol-4yl)oxy)acetic acid, its sodium salt, and methyl ester.

Proportion and Weight of Active Compounds used in the Method of the Invention

The 1H-indole-3-glyoxylamide compound may be used at a concentration of 0.1 to 99.9 weight percent of the formulation.

Preferably the pharmaceutical formulation is in unit dosage form. The unit dosage form can be a capsule or tablet itself, or the appropriate number of any of these. The quantity of active compound in a unit dose of composition may be varied or adjusted from about 0.1 to about 1000 milligrams or more according to the particular treatment involved.

Compositions (dosage forms) suitable for internal administration contain from about 1 milligram to about 500 milligrams of active compound per unit. In these pharmaceutical compositions the active compound will ordinarily be present in an amount of about 0.5–95% by weight based on the total weight of the composition.

Examples of useful pharmaceutical compositions and their proportions of ingredients are illustrated as follows:

Capsules: Capsules may be prepared by filling standard two-piece hard gelatin capsules each with 50 mg of powdered active compound, 175 mg of lactose, 24 mg of talc, and 6 mg of magnesium stearate.

Soft Gelatin Capsules: A mixture of active compound in soybean oil is prepared and injected by means of a positive displacement pump into gelatin to form soft gelatin capsules containing 50 mg of the active compound. The capsules are washed in petroleum ether and dried.

Tablets: Tablets may be prepared by conventional procedures so that the dosage unit is 50 mg of active compound, 6 mg of magnesium stearate, 70 mg of microcrystalline cellulose, 11 mg of cornstarch, and 225 mg of lactose. Appropriate coatings may be applied to increase palatability or delay absorption.

Suspensions: An aqueous suspension is prepared for oral administration so that each 5 ml contain 25 mg of finely divided active compound, 200 mg of sodium carboxymethyl cellulose, 5 mg of sodium benzoate, 1.0 g of sorbitol solution, U.S.P., and 0.025 mg of vanillin.

Injectables: A parenteral composition suitable for administration by injection is prepared by stirring 1.5% by weight of active compound in 10% by volume propylene glycol and water. The solution is sterilized by commonly used techniques.

Nasal Spray: An aqueous solution is prepared such that each 1 ml contains 10 mg of active compound, 1.8 mg methylparaben, 0.2 mg propylparaben and 10 mg methylcellulose. The solution is dispensed into 1 ml vials. The active compound may be used at a concentration of 0.1 to 99.9 weight percent of the formulation.

Aerosol formulations are capable of dispersing into particle sizes of from about 0.5 to about 10 microns and have sufficient sPLA2 inhibitor to achieve concentrations of the inhibitor on the airway surfaces of from about $10^{-10}$ to $10^{-2}$ moles per liter.

Suppositiories: Compounds contemplated for use in the practice of the present invention may also be administered in the form of suppositories for rectal administration of the drug. These compositions may be prepared, for example, by intimate admixture of the active ingredient with the carrier, preferably the molten carrier. Preferably the active ingredient is milled or sieved prior to incorporation into the molten carrier. The molten composition may then be poured into suitable molds. Optionally the suppositories may be coated prior to packing, for, with cetyl alcohol, macrogol or polyvinyl alcohol and polysorbates to increase disintegration time or lubrication.

The Practice of the Method of the Invention

The use of $sPLA_2$ inhibitors in the method of the invention prevents progressive deterioration of colonic and intestinal tissue and function by inhibiting or reducing the degree of inflammation which may be a primary pathologic process in inflammatory bowel disease. The method of the invention is preferably used early in the life of the patient afflicted with inflammatory bowel disease.

The method of the invention can be practiced using pharmaceutical formulations containing $sPLA_2$ inhibitors (preferably, $sPLA_2$ inhibitors taught to be preferred in this specification) or formulations containing such $sPLA_2$ inhibitors as taught in the preceding section.

In some cases the underlying cause of inflammatory bowel disease will not be prevented by the method of this invention, but symptoms will be reduced in severity or extent ameliorated by administration of $sPLA_2$ inhibitors (and their formulations).

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active compound can be about 0.1 to 200 milligrams per kilogram of body weight. Ordinarily 0.5 to 50, and preferably 1 to 25 milligrams per kilogram per day given in divided doses 1 to 6 times a day or in sustained release form is effective to obtain desired results.

In general, the $sPLA_2$ inhibitor will be administered to a human so that a therapeutically effective amount is received. A therapeutically effective amount may conventionally be determined for an individual patient by administering the active compound in increasing doses and observing the effect on the patient, for example, reduction in the severity of inflammation, reduction in bleeding, stoppage of diarrhea, amelioration of intestinal obstruction, or a reduction in other symptoms associated with inflammatory bowel disease.

Generally, the compound must be administered in a manner and a dose to achieve in the human a blood level concentration of $sPLA_2$ inhibitor of from 10 to 3000 nanograms/ml, and preferably a concentration of 100 to 800 nanograms/ml.

The treatment regimen for inflammatory bowel disease may stretch over many days to months or to years. Oral dosing is preferred for patient convenience and tolerance. With oral dosing, one to four oral doses per day, each from about 0.01 to 25 mg/kg of body weight with preferred doses being from about 0.1 mg/kg to about 2 mg/kg.

Parenteral administration (particularly, intravenous administration) is often preferred in instances where rapid alleviation of patient distress is required. With parenteral administration doses of 0.01 to 100 mg/kg/day administered continuously or intermittently throughout the day may be used. For parenteral administration, the compound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose).

CO-Agent—Combined Therapy

The sPLA$_2$ inhibitor (viz., active compound in a formulation of the invention) can also be administered in the method of the invention in combination with another pharmacologically active agent known to have utility for alleviating the symptoms of inflammatory bowel disease. For example, the sPLA$_2$ inhibitors taught herein may be combined with the following therapeutic agents:

1. Anti-inflammatory agents, e.g. sulfasalazine
2. Agents that control intestinal tract infection
   a. antibiotics
      (i) penicillins, for example bacitracin
      (ii) glycopeptides, for example vancomycin
3. Steroids (glucorticosteroids)
4. Immunosupressive agents, for example azathioprine
5. Agents for controlling diarrhea, for example cholestryramine Testing Methods for Inflammatory Bowel Disease The diagnostic criteria for inflammatory bowel disease are those found in standard medical references (e.g., Harrison's Principles of Internal Medicine, thirteenth ed., 1994, by McGraw-Hill, Inc., ISBN 0-07-032370-4, pgs., 1194–1197). These criteria may be used to determine when to begin using the method of the invention, the frequency and degree of treatment, and the time for cessation of treatment.

While the present invention has been illustrated above by certain specific embodiments, these are not intended to limit the scope of the invention as described in the appended claims.

I claim:

1. A formulation for treating IBD comprising:

A. 1H-indole-3-glyoxylamide represented by formula

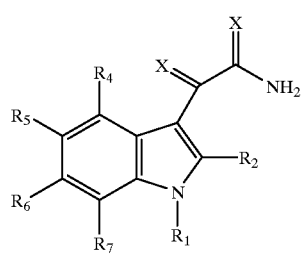

(I)

wherein;

both x are oxygen;

$R_1$ is selected from the group consisting of

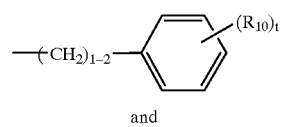

and

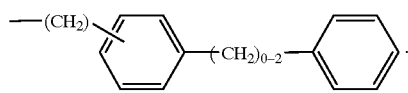

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)-(acidic group); wherein —($L_a$)— is an acid linker; provided, the acid linker group, —($L_a$)—, for $R_4$ is selected from the group consisting of;

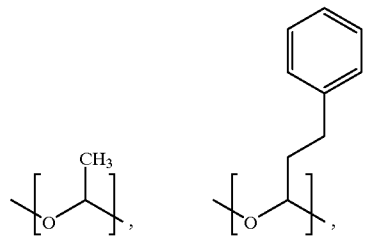

and provided, the acid linker, —($L_a$)—, for $R_5$ is selected from group consisting of;

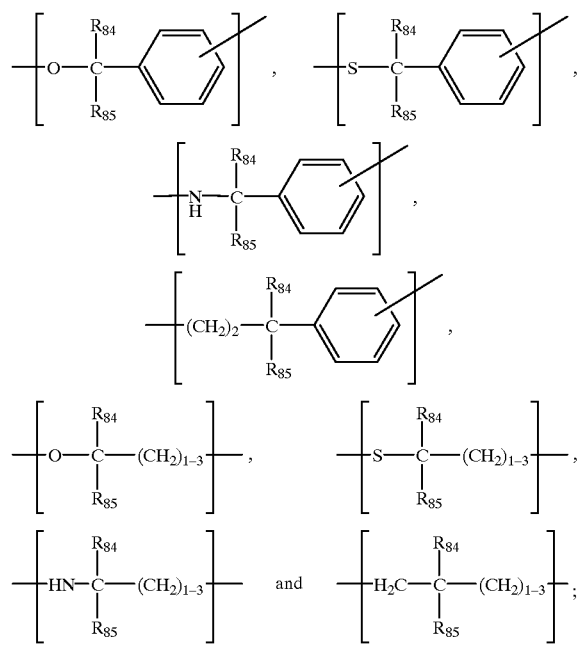

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)-(acidic group) and wherein the (acidic group) on the group —($L_a$)-(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, phenylmethyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O—(C$_1$-C$_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$-C$_6$ carbonyl; where n is from 1 to 8 or a pharmaceutically acceptable salt or aliphatic ester prodrug derivative thereof; and B) one or more co-agents other than sPLA$_2$ inhibitors selected from the group consisting of:
a. anti-inflammatory agents,
b. antibiotics,
c. steroids,
d. immunosuppressor agents, and
e. diarrhea controlling agents:

C) optionally, a carrier or diluent.

2. The formulation of claim 1 wherein the weight ratio of (A) to (B) is from 1:100 to 100:1.

3. The formulation of claim 1 wherein the weight ratio of (C) to the sum of (A) and (B) is from 1:50 to 50:1.

4. A method of treating IBD by administering to a mammal in need thereof a therapeutically effective amount of the formulation of claim 1.

5. A method for treating a mammal afflicted with IBD, said method comprising administering to said mammal in need of such treatment, a therapeutically effective amount of a 1H-indole-3-glyoxylamide of the invention represented by the formula (I), or a pharmaceutically acceptable salt or aliphatic ester prodrug derivative thereof;

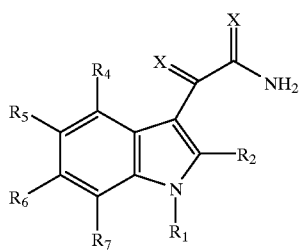

(I)

wherein;
both X are oxygen;
R$_1$ is selected from the group consisting of

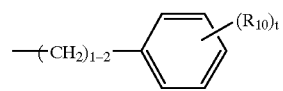

and

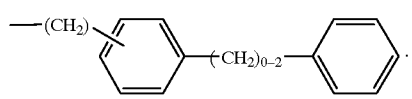

where R$_{10}$ is a radical independently selected from halo, C$_1$-C$_{10}$ alkyl, C$_1$-C$_{10}$ alkoxy, —S—(C$_1$-C$_{10}$ alkyl), and C$_1$-C$_{10}$ haloalkyl and t is a number from 0 to 5;
R$_2$ is selected from the group; halo, cyclopropyl, methyl, ethyl, and propyl;
R$_4$ and R$_5$ are independently selected from hydrogen, a non-interfering substituent, or the group, —(L$_a$)-(acidic group); wherein —(L$_a$)— is an acid linker; provided, the acid linker group, —(L$_a$)—, for R$_4$ is selected from the group consisting of;

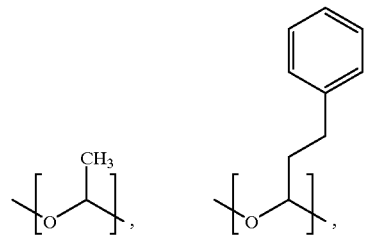

and provided, the acid linker, —(L$_a$)—, for R$_5$ is selected from group consisting of;

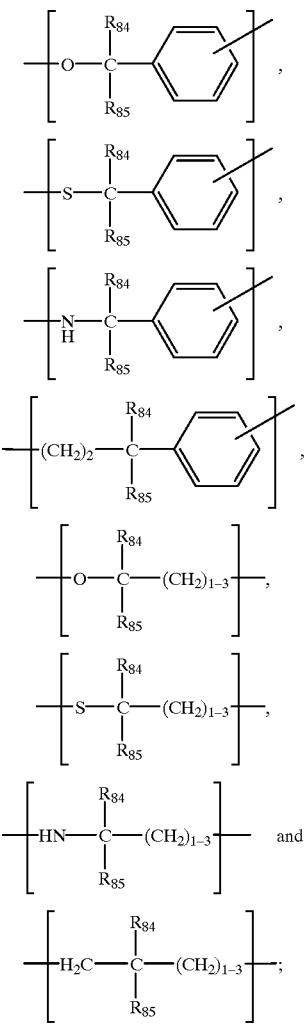

wherein R$_{84}$ and R$_{85}$ are each independently selected from hydrogen, C$_1$-C$_{10}$ alkyl, aryl, C$_1$-C$_{10}$ alkaryl, C$_1$-C$_{10}$ aralkyl, carboxy, carbalkoxy, and halo; and
provided, that at least one of R$_4$ and R$_5$ must be the group, —(L$_a$)-(acidic group) and wherein the (acidic group) on the group —(L$_a$)-(acidic group) of R$_4$ or R$_5$ is selected from —CO$_2$H, —SO$_3$H, or —P(O) (OH)$_2$;
R$_6$ and R$_7$ are each independently selected form hydrogen and non-interfering substituents, with the non-interfering substituents being selected from the group consisting of the following: $C_1-C_6$ alkyl, $C_2-C_6$ alkenyl, $C_2-C_6$ alkynyl, $C_7-C_{12}$ aralkyl, $C_7-C_{12}$ alkaryl, $C_3-C_8$ cycloalkyl, $C_3-C_8$ cycloalkenyl, phenyl, tolulyl, xylenyl, phenylmethyl, $C_1-C_6$ alkoxy, $C_2-C_6$ alkenyloxy, $C_2-C_6$ alkynyloxy, $C_2-C_{12}$ alkoxyalkyl, $C_2-C_{12}$ alkoxyalkyloxy, $C_2-C_{12}$ alkylcarbonyl, $C_2-C_{12}$ alkylcarbonylamino, $C_2-C_{12}$ alkoxyamino, $C_2-C_{12}$ alkoxyaminocarbonyl, $C_2-C_{12}$ alkylamino, $C_1-C_6$ alkylthio, $C_2-C_{12}$ alkylthiocarbonyl, $C_1-C_6$ alkylsulfinyl, $C_1-C_6$ alkylsulfonyl, $C_2-C_6$ haloalkoxy, $C_1-C_6$ haloalkylsulfonyl, $C_2-C_6$ haloalkyl, $C_1-C_6$ hydroxyalkyl, —C(O)O($C_1-C_6$ alkyl), —(CH$_2$)$_n$—O—($C_1-C_6$ alkyl), benzyloxy, phenoxy, phenylthio, —(CONHSO$_2$R), —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1-C_6$ carbonyl; where n is from 1 to 8.

6. A method for treatment of a human afflicted with inflammatory bowel disease, said method comprising administering to said human in need of such treatment, a therapeutically effective amount of a 1H-indole-3-glyoxylamide compound or a pharmaceutically acceptable salt, solvate, or a prodrug derivative thereof, for the treatment of IBD, selected from the group consisting of compounds (A) through (P):

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid,
(G) [[3-(2-Amino-1,2-dioxoethyl)-1-[4(-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (O).

7. A method for treatment of a human afflicted with inflammatory bowel disease, said method comprising administering to said human in need of such treatment a therapeutically effective amount of a 1H-indole-3-glyoxylamide compound selected from the group consisting of compounds represented by the formulae:

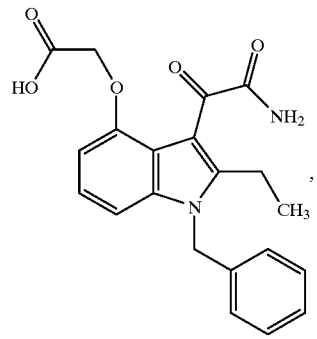

(Va)

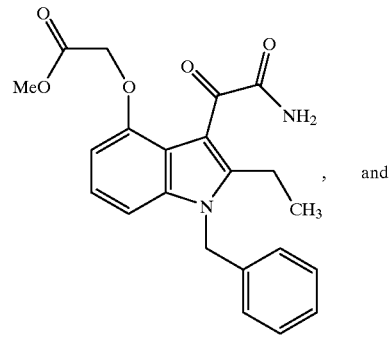

(Vb)

, and

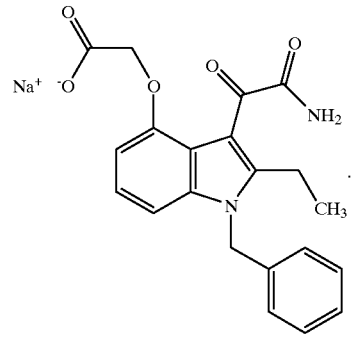

(Vc)

8. The method as in any one of claim 5 or 6 or 7 wherein the administration of the 1H-indole-3-glyoxylamide is intravenous.

9. The method as in any one of claim 5 or 6 or 7 wherein the administration of the 1H-indole-3-glyoxylamide is oral.

10. The method as in any one of claim 5 or 6 or 7 wherein treatment is of a human afflicted with inflammatory bowel disease and the 1H-indole-3-glyoxylamide inhibitor is administered in a therapeutically effective amount to achieve a human blood level inhibitor concentration of from 10 to 3000 nanograms/ml.

11. The method as in any one of claim 5 or 6 or 7 wherein administration of the 1H-indole-3-glyoxylamide is in an amount of from 0.01 mg/kg/day to 100 mg/kg/day.

12. The method as in any one of claim 5 or 6 or 7 wherein the therapeutically effective amount of the 1H-indole-3-glyoxylamide is in the form of a pharmaceutical formulation comprising the 1H-indole-3-glyoxylamide compound and a suitable carrier or excipient therefor.

* * * * *

UNITED STATES PATENT AND TRADEMARK OFFICE
CERTIFICATE OF CORRECTION

PATENT NO. : 6,340,699 B1
DATED : January 22, 2002
INVENTOR(S) : William Louis Macias It is certified that error appears in the above-identified patent and that said Letters Patent is hereby corrected as shown below:

Column 16,
Line 4, delete the chemical structures and insert the following chemical structures therefore:

--

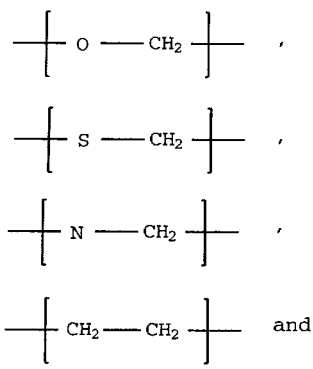

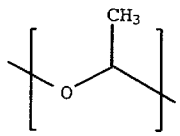 ,

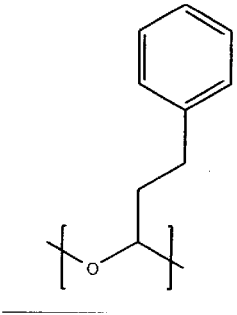 ,

--

UNITED STATES PATENT AND TRADEMARK OFFICE
CERTIFICATE OF CORRECTION

PATENT NO. : 6,340,699 B1
DATED : January 22, 2002
INVENTOR(S) : William Louis Macias It is certified that error appears in the above-identified patent and that said Letters Patent is hereby corrected as shown below:

Column 18,
Line 3, delete the chemical structures and insert the following chemical structures therefore:

--

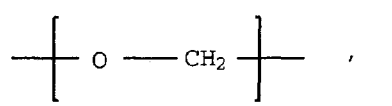 ,

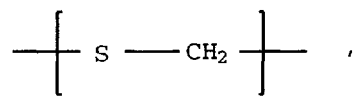 ,

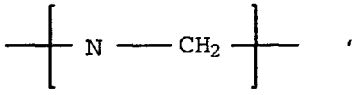 ,

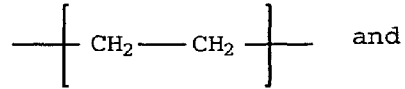 and

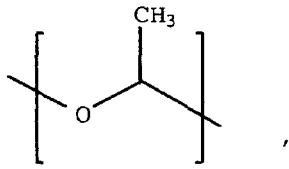 ,

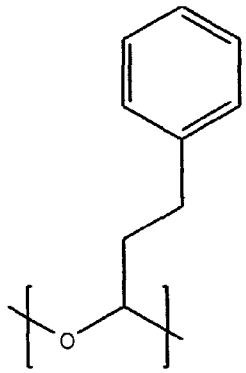 ,

--

UNITED STATES PATENT AND TRADEMARK OFFICE
CERTIFICATE OF CORRECTION

PATENT NO. : 6,340,699 B1
DATED : January 22, 2002
INVENTOR(S) : William Louis Macias It is certified that error appears in the above-identified patent and that said Letters Patent is hereby corrected as shown below:

Column 20,
Line 47, delete "of the 1H-indole-3-glyoxylamide" and insert -- of 1H-indole-3-glyoxylamide -- therefore.
Line 50, delete "of the 1H-indole-3-glyoxylamide" and insert -- of 1H-indole-3-glyoxylamide -- therefore.
Line 58, delete "of the 1H-indole-3-glyoxylamide" and insert -- of 1H-indole-3-glyoxylamide -- therefore.
Line 61, delete "of the 1H-indole-3-glyoxylamide" and insert -- of 1H-indole-3-glyoxylamide -- therefore.

Signed and Sealed this

Nineteenth Day of November, 2002

Attest:

JAMES E. ROGAN
Attesting Officer
Director of the United States Patent and Trademark Office